(12) United States Patent
Blakley et al.

(10) Patent No.: US 6,830,046 B2
(45) Date of Patent: Dec. 14, 2004

(54) METERED DOSE INHALER

(75) Inventors: Daniel Robert Blakley, Philomath, OR (US); Daniel Beeton, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 62 days.

(21) Appl. No.: 10/136,005

(22) Filed: Apr. 29, 2002

(65) Prior Publication Data
US 2003/0200964 A1 Oct. 30, 2003

(51) Int. Cl.[7] ............................................. A61M 11/00
(52) U.S. Cl. ........................ 128/200.14; 128/200.16; 128/204.21; 128/203.12
(58) Field of Search ....................... 128/200.14, 200.16, 128/202.22, 204.21, 205.23, 203.12

(56) References Cited

U.S. PATENT DOCUMENTS

| | | | |
|---|---|---|---|
| 4,495,944 A | * | 1/1985 | Brisson et al. ............... 600/538 |
| 4,934,358 A | * | 6/1990 | Nilsson et al. ......... 128/200.23 |
| 4,967,208 A | | 10/1990 | Childers |
| 4,984,158 A | * | 1/1991 | Hillsman ............... 128/200.14 |
| 5,002,048 A | * | 3/1991 | Makiej, Jr. ............. 128/200.23 |
| 5,007,419 A | * | 4/1991 | Weinstein et al. ..... 128/200.23 |
| 5,167,506 A | * | 12/1992 | Kilis et al. ................... 434/262 |
| 5,169,029 A | * | 12/1992 | Behar et al. ..................... 222/1 |
| 5,284,133 A | | 2/1994 | Burns et al. |
| 5,331,953 A | | 7/1994 | Andersson et al. |
| 5,363,842 A | * | 11/1994 | Mishelevich et al. .. 128/200.14 |
| 5,404,871 A | * | 4/1995 | Goodman et al. ..... 128/200.14 |
| 5,437,267 A | * | 8/1995 | Weinstein et al. ..... 128/200.23 |
| 5,450,336 A | | 9/1995 | Rubsamen et al. |
| 5,452,711 A | * | 9/1995 | Gault ..................... 128/200.14 |
| 5,551,416 A | * | 9/1996 | Stimpson et al. ...... 128/200.16 |
| 5,664,557 A | * | 9/1997 | Makiej, Jr. ............. 128/200.23 |
| 5,676,129 A | | 10/1997 | Rocci, Jr. et al. |
| 5,724,957 A | | 3/1998 | Rubsamen et al. |
| 5,813,397 A | * | 9/1998 | Goodman et al. ..... 128/200.14 |
| 5,830,490 A | * | 11/1998 | Weinstein et al. .......... 424/405 |
| 5,881,716 A | | 3/1999 | Wirch et al. |
| 5,894,841 A | | 4/1999 | Voges |
| 5,925,021 A | | 7/1999 | Castellano et al. |
| 5,931,160 A | * | 8/1999 | Gilmore et al. ........ 128/204.21 |
| 5,941,240 A | | 8/1999 | Gonda et al. |
| 5,941,241 A | * | 8/1999 | Weinstein et al. ..... 128/200.23 |
| 5,950,619 A | * | 9/1999 | van der Linden et al. ...................... 128/200.16 |
| 6,029,659 A | | 2/2000 | O'Connor |
| 6,131,566 A | | 10/2000 | Ashurst et al. |
| 6,138,669 A | | 10/2000 | Rocci, Jr. et al. |
| 6,162,443 A | | 12/2000 | Flament-Garcia et al. |
| 6,186,956 B1 | | 2/2001 | McNamee |
| 6,192,882 B1 | | 2/2001 | Gonda |
| 6,202,642 B1 | * | 3/2001 | McKinnon et al. .... 128/200.23 |
| 6,220,243 B1 | | 4/2001 | Schaeffer et al. |
| 6,221,653 B1 | | 4/2001 | Caren et al. |
| 6,223,746 B1 | | 5/2001 | Jewett et al. |
| 6,257,690 B1 | | 7/2001 | Holstun |
| 6,280,012 B1 | | 8/2001 | Schloeman et al. |
| 6,382,205 B1 | * | 5/2002 | Weinstein et al. ..... 128/200.23 |
| 6,435,175 B1 | * | 8/2002 | Stenzler ................. 128/200.14 |
| 6,523,536 B2 | * | 2/2003 | Fugelsang et al. ..... 128/200.14 |
| 6,543,443 B1 | * | 4/2003 | Klimowicz et al. .... 128/200.23 |
| 6,571,790 B1 | * | 6/2003 | Weinstein .............. 128/200.19 |

FOREIGN PATENT DOCUMENTS

WO    WO 00/53247    9/2000

\* cited by examiner

Primary Examiner—Aaron J. Lewis

(57) ABSTRACT

The present invention provides a metered dose inhaler including an ejection mechanism with at least one chamber for containing a medicament. The ejection mechanism is configured to effect controlled ejection of the medicament from the chamber. The inhaler further includes a controller configured to send electronic signals to the ejection mechanism to direct ejection of medicament from such chamber, and configured to selectively alter dosage of the medicament by selected changes in such electronic signal.

50 Claims, 4 Drawing Sheets

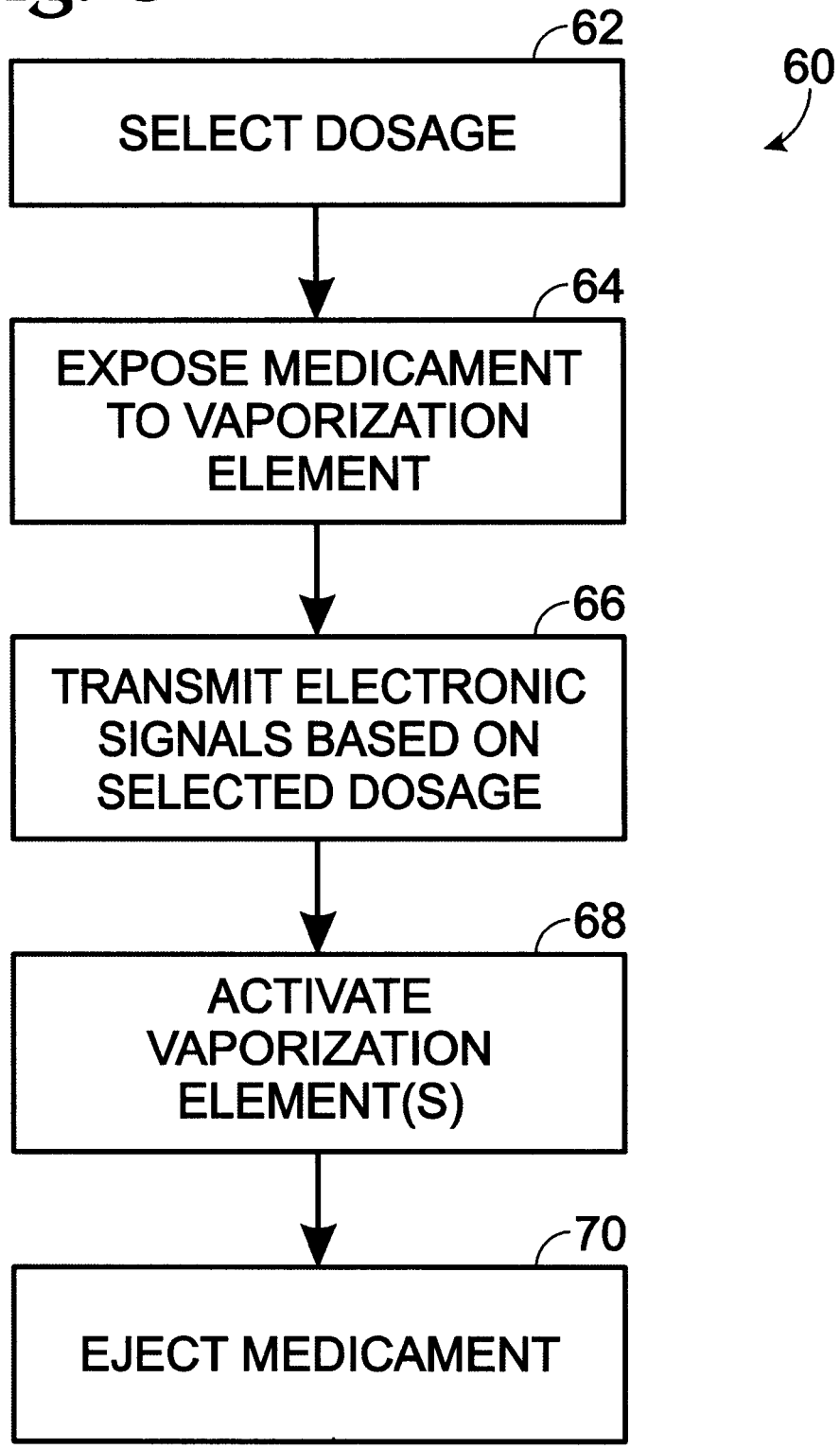

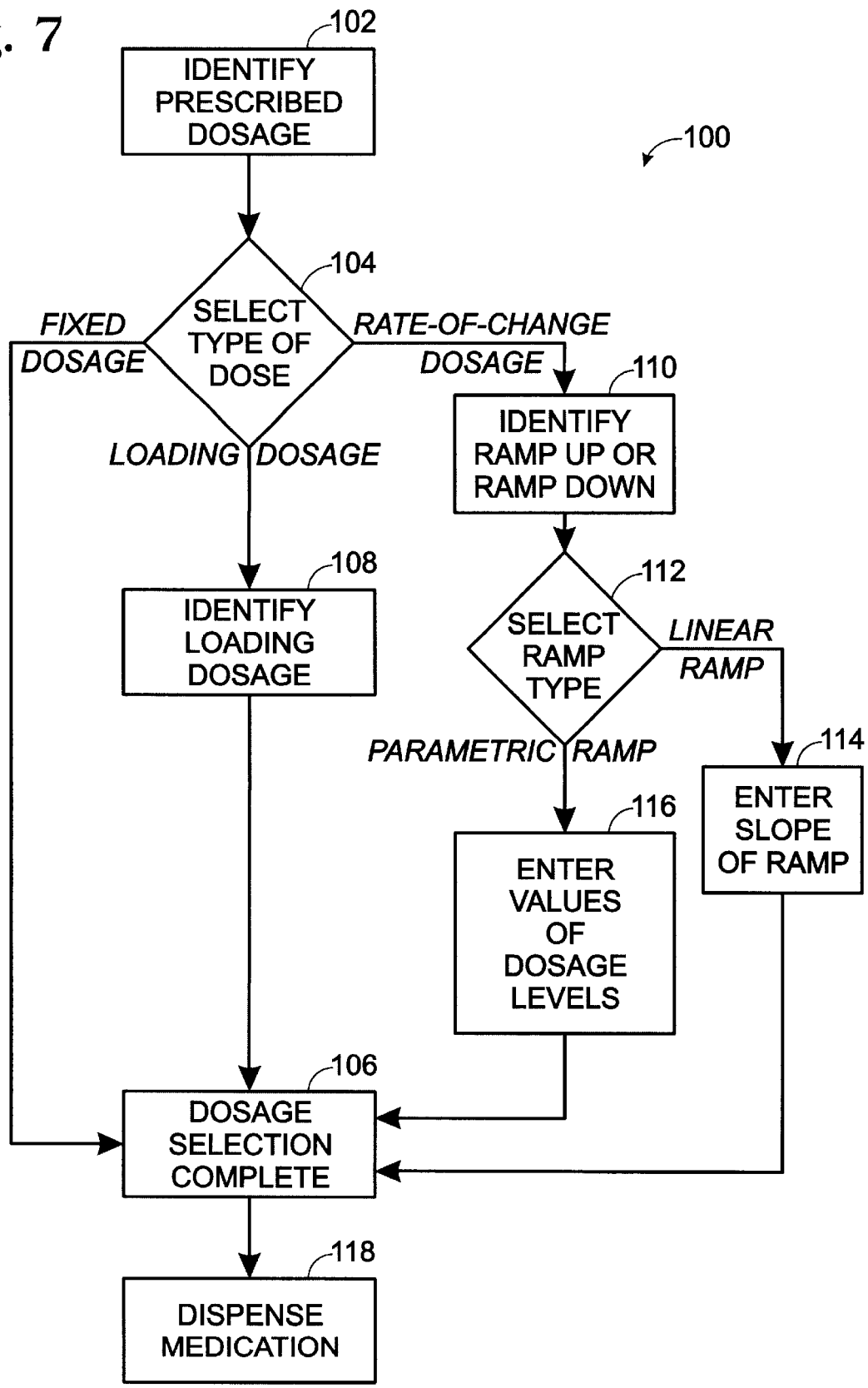

METERED DOSE INHALER

BACKGROUND OF THE INVENTION

Metered dose inhalers provide a much-needed drug-delivery method that allows patients to aspirate medication rather than swallow a pill, or drink or inject medication. In some cases, as with medications that directly target the patient's lungs, aspiration enables the medicine to reach the target area more quickly. In addition, aspiration is typically considered to be less painful than other drug-delivery methods.

Known metered dose inhalers typically include a pressurized cartridge containing an inhalant mixed with an aerosol propellant or carrier. The user places the inhaler's mouthpiece in or over his mouth and/or nose and activates the inhaler, typically by mechanical opening of an atomizing valve. Activation of the inhaler thus releases a "puff" of the inhalant-propellant mixture, which the user then aspirates through his mouth and/or nose.

The use of a pressurized cartridge can be problematic if the cartridge is ever breached. Because the contents of the cartridge are under pressure, a crack or break in the cartridge can lead to an unintended release of the inhalant, possibly without the user's knowledge. This may increase costs to the patient, who may be forced to pay to replace lost medication, and can lead to unintentional dosing. This may be a significant concern as one use of inhalers is to allow patients to self-administer pain medications for which unintentional dosing may have serious consequences.

Furthermore, in some cases, it may be undesirable to maintain the medication in an aerosol carrier, or to administer medication with a chemical propellant. Many metered dose inhalers use chlorofluorocarbons (CFCs) as their propellant. The CFCs are inhaled by the patient, and then quickly eliminated by the body and released into the atmosphere. Due to environmental concerns raised by the use of CFCs, there have been recent governmental mandates to reduce and/or eliminate the use of CFCs in commercial products. Metered dose inhalers are one of the few products to have received a reprieve from these governmental mandates due to the lack of suitable replacements and the severity of the consequences if metered dose inhalers were to be removed from the market. Nevertheless, because a portion of each puff is propellant, the use of a propellant carrier may make dosage more inaccurate. For example, for medications requiring a very specific dosage, any variation in the ratio of propellant to medication may affect the efficacy of the medication.

Moreover, it has been shown that maximum effectiveness of pulmonary inhalation occurs over a rather limited range of droplet diameter sizes. These maximum effective sizes typically are in a range of 5 to 8 microns. Known metered dose inhalers may produce a large range of droplet sizes within a single puff, including droplets both above and below the ideal range. Those droplets that are too small are not retained by the lungs, and are instead exhaled out of the body. Likewise, those droplets that are too large are not absorbed by the lungs, and are also exhaled out of the body.

Finally, known inhalers have been limited to a single dosage. Typically, the only way to alter the dosage of a medication that is administered by an inhaler has been to either prescribe more than one "puff", or to prescribe a different-sized inhaler. Either of these situations may be undesirable, particularly if a patient wishes to decrease dosage during a treatment regime, for example, due to unwanted side effects from the medication. Thus, in some cases, it may be desirable to allow the patient to vary dosage (within a safe range). Alternatively, or additionally, it may be desirable to allow the doctor or pharmacist to alter the dosage during the course of treatment, for example, to provide a loading dose, or to ramp-up or ramp-down the amount of medication administered during the treatment regime.

SUMMARY OF THE INVENTION

The present invention provides a metered dose inhaler including an ejection mechanism with at least one chamber for containing a medicament. The ejection mechanism is configured to effect controlled ejection of medicament from the chamber. The inhaler further includes a controller configured to send an electronic signal to the ejection mechanism to direct ejection of medicament from the chamber, and configured to selectively alter dosage of the medicament by selected changes in such electronic signal.

BRIEF DESCRIPTION OF THE DRAWINGS

FIG. 5 is a flow chart demonstrating a method of administering a medicament to a patient in accordance with one embodiment of the present invention.

FIG. 7 is a flow chart illustrating methodology by which a physician or pharmacist may regulate a dosage administered by a metered dose inhaler.

DETAILED DESCRIPTION OF THE PREFERRED EMBODIMENT

Figure 1:
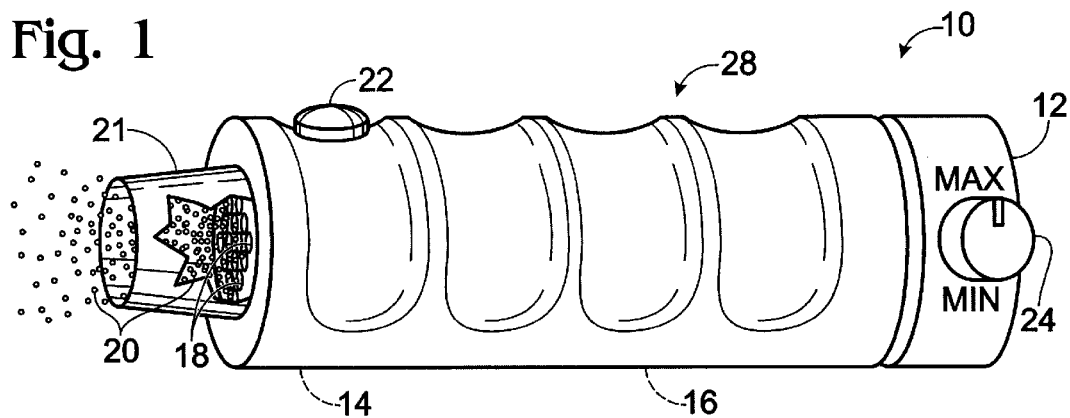
FIG. 1 is a side view of a metered dose inhaler according to one embodiment of the present invention.
Figure 4:
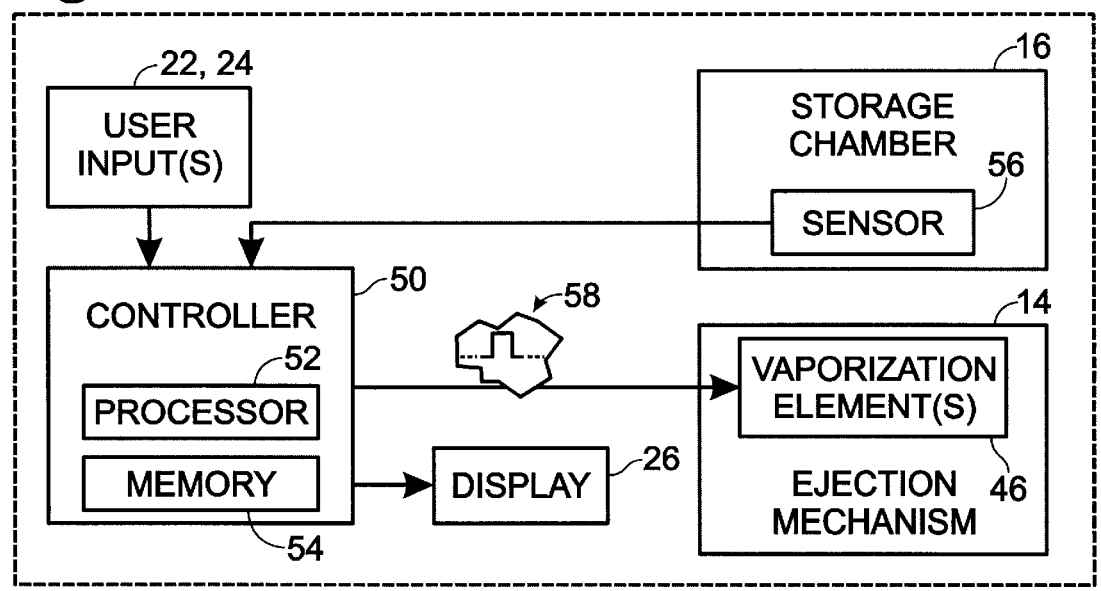
FIG. 4 is a block diagram of the metered dose inhaler of FIG. 1.

One embodiment of the present invention is shown in side view and partial cut-away in FIG. 1. Inhaler 10 includes a body 12 having an ejection mechanism 14 in fluid communication with a medicament storage chamber 16. As will be appreciated upon reading further, ejection mechanism 14 may be configured to effect ejection of a selected dosage of medicament/inhalant from inhaler 10 in response to a signal sent by a controller (described below with reference to FIG. 4). Suitable medicaments include those typically found in liquid, solid, powder, paste or other forms.

Focusing initially on ejection of the medicament, it is to be understood that ejection mechanism 14 typically will include a vaporization region with one or more ejection chambers, each with an element configured to eject vaporized droplets of medicament in a manner described in greater detail with respect to FIG. 3 below. As indicated, this region may define a plurality of orifices 18 which produce the vaporized, or atomized, droplets of medicament in an inhalant stream 20.

Orifices 18 may feed into a mouthpiece 21, which may be placed in the patient's mouth in order to facilitate administration of the medicament to the patient in what is referred to herein as a dosing event. As will be appreciated, however, mouthpiece 21 may take alternative forms, including forms which may be adapted to fit over a patient's mouth and/or nose.

Inhaler 10 may further include one or more user inputs which facilitate communication between the user and the inhaler's controller. This communication may include directives and/or information communicated from the user to the controller, and vice versa. For example, activation input 22 may be configured to communicate a directive from the user to the controller to initiate a dosing event. In the present invention, activation input 22 takes the form of a depressible button, as shown in FIG. 1, but could take the form of a trigger, switch, touch-sensitive button, or the like. Activation input 22 is located on top of body 12, but it will be appreciated that such input may be positioned in virtually any other location convenient to the user.

Another user input is shown at 24 in the form of dose size regulator 24, which may be used to modify or alter the dosage produced by the inhaler, as will be described in further detail below. For the purpose of the present disclosure, the inhaler's dosage shall be defined as the total volume of medicament/inhalant ejected by the inhaler during a single dosing event, e.g., the total amount of medication released over a period of time corresponding to a single "puff" by the user. As will be appreciated, dosage, and the degree to which it may be varied safely, may depend on the type of medication being disseminated and the needs of a particular user/patient.

Other forms of user inputs alternatively, or additionally, may be provided to direct operation of the inhaler, or otherwise facilitate communication between the user (or health care professional) and the controller (or other features of inhaler 10). The controller, for example, may be adapted for communication with a personal computer or other device to accommodate initial dosage programming of the inhaler, and/or to accommodate appropriate security measures when programming or using the inhaler. The controller thus may be adapted to permit changes in dosage by the user within acceptable parameters as determined by a pharmacist or prescribing physician as will be described further below.

Figure 2:
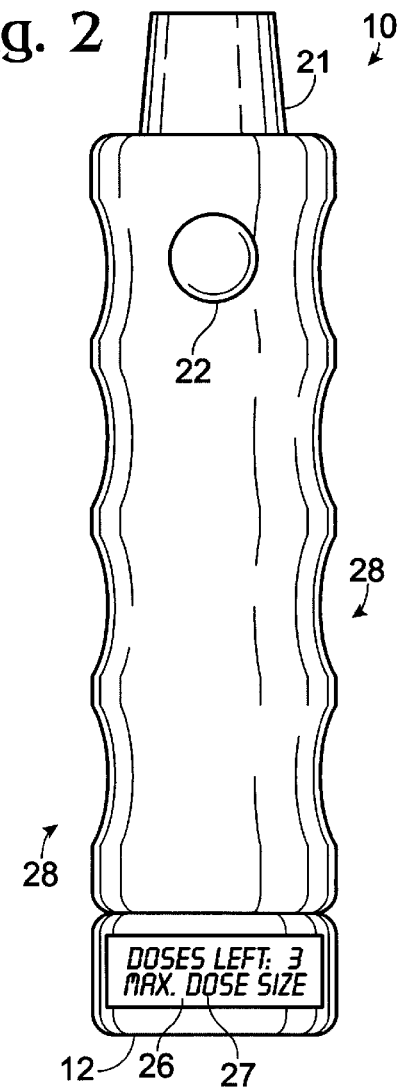
FIG. 2 is a top view of the metered dose inhaler of FIG. 1.

FIG. 2 is a top view of inhaler 10, showing a display 26 which may be, for example, an LCD display adapted to display information to the user. It will be appreciated, however, that it is not necessary for the display to be an electronic display. For example, the display may take the form of a mechanical counter, a mechanical gauge, or some other suitable device.

Typically, display 26 is adapted to provide the user with dosage information 27, such as the number of doses administered and/or the number of doses remaining in the inhaler. In some instances, however, display 26 may also be adapted to provide the user with information such as patient name, patient identification number, prescribing physician name, prescribing physician identification number, type of medication, recommended dosage, dose regimen, available alterations to the recommended dosage and/or dose regimen, etc. As will be appreciated, display 26 may be located in any convenient location on body 12. Moreover, display 26 may enable two-way communication between the user and the inhaler, for example, through use of a touch screen or other device. Thus, display 26 may itself serve as a user input, similar to inputs 22 and 24 described above.

As further shown in FIG. 2, body 12 may be shaped to provide gripping regions 28 so as to accommodate the hand and/or fingers of the user. As will be appreciated, alternative configurations of inhaler 10 are contemplated by the present invention, including those more closely resembling traditional L-shaped metered dose inhalers, wherein the medicament storage chamber is located in an upright fashion, generally perpendicular to the mouthpiece.

Figure 3:
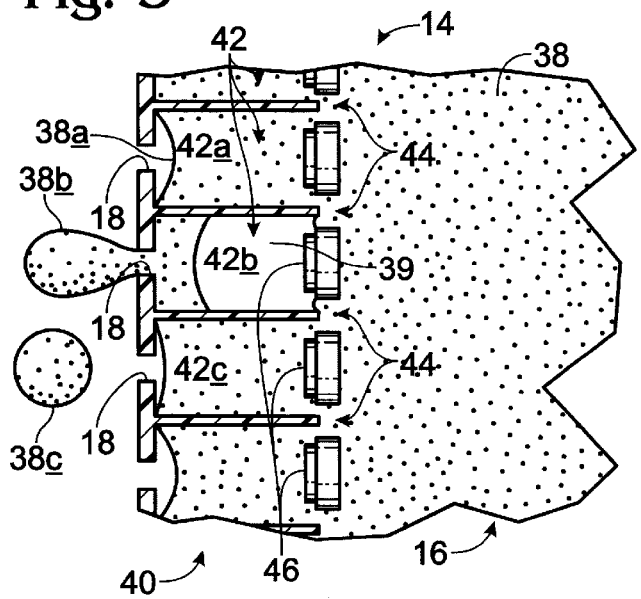
FIG. 3 is a somewhat schematic illustration of an ejection mechanism according to one embodiment of the invention.

Turning now to FIG. 3, a somewhat schematic fragmentary illustration of one possible interior configuration of inhaler 10 is depicted, the illustration being confined generally to the vicinity of ejection mechanism 14. As previously stated, ejection mechanism 14 is in fluid communication with medicament storage chamber 16, which may serve to house medicament 38 prior to dosing. In accordance with its proposed operation, the ejection mechanism includes a vaporization region 40, which may be configured to accommodate vaporization, or atomization, of medicament 38.

In the embodiment shown in FIG. 3, vaporization region 40 includes a plurality of ejection chambers 42, each in fluid communication with medicament storage chamber 16, for example, via fluid channels 44. Passage of the medicament 38 from the medicament storage chamber 16 to ejection chambers 42 may be either active or passive. For example, ejection of medicament within an ejection chamber may itself produce a vacuum sufficient to draw more medicament into the ejection chamber. Alternatively, gravity, or more active forms of transportation, including pumps or other mechanical or electronic means may be employed. These ejection chambers are also referred to as vaporization chambers for reasons which will become apparent upon reading further.

The ejection chambers are each adapted to receive and contain a charge of fluid medicament, as indicated for example, in uppermost ejection chamber 42*a*. This may be accomplished, in part, due to the geometry of the ejection chamber, which may lead to formation of a meniscus 38*a* adjacent the chamber's ejection orifice. The ejection chambers, it will be appreciated, open to the inhaler mouthpiece via ejection orifices 18, but typically do not freely pass medicament through the orifices due to menisci such as that shown at 38*a*.

Each ejection chamber will be seen to include at least one ejection element 46 configured to selectively controllably eject medicament from within the corresponding ejection chamber as a vaporized medicament droplet. In the present embodiment, the ejection element (also referred to as a vaporization element) takes the form of a heating element opposite the chamber's ejection orifice. In response to an ejection signal (e.g., a predetermined voltage applied across a heating element), the heating element is activated, heating medicament in the vicinity thereof. Such heated medicament, in turn, expands toward the ejection orifice, overcoming opposing forces of the meniscus and forcing more distal medicament out of the ejection orifice in a predicable-size vapor droplet. Such ejection is demonstrated in FIG. 3 in connection with ejection chamber 42*b*.

In ejection chamber 42*b*, the ejection element will be seen to superheat medicament in its vicinity to produce a bubble 39 which is shown expanding toward the ejection orifice. The advancing bubble, in turn, will be seen to urge medicament which was previously within ejection chamber 42*b* out through the ejection orifice so as to form a vapor droplet 38*b*. The size and trajectory of this ejected vapor droplet may be reliably predicted based on the size and shape of ejection chamber 42*b*, as well as the power dissipated in the chamber.

As indicated in connection with ejection chamber 42*c* of FIG. 3, once a vapor droplet (e.g. 38*c*) has been ejected, and the ejection element deactivated (e.g. cooled), medicament may again flow into the ejection chamber, effectively filling the ejection chamber with a new charge of medicament upon formation of a meniscus adjacent the ejection orifice.

Ejection element 46 may take any of various forms, including for example, a resistor capable of independent activation by the inhaler's controller. When the resistor of a particular ejection chamber receives an electronic signal from the controller, the resistor may produce sufficient heat to eject a medicament vapor droplet from the corresponding ejection chamber. Such chamber activation typically occurs repetitively and in rapid succession. Ejection elements 46 may also take the form of a piezoelectric transducers. Correspondingly, when the transducer receives an electronic signal from the controller, the transducer may produce enough voltage to eject medicament from within the ejection chamber. In either case, the presently-described metered dose inhaler is able to produce an inhalant stream without the use of an aerosol carrier or propellant.

Ejection elements may be controlled independently, as alluded to above, or may be controlled in groupings or subsets of a full set. By electronically controlling the rate of ejection element activation, it is possible to control the rate of medicament ejection, and thus the medicament dosage produced by the inhaler. This may be accomplished whether the vaporization elements are controlled together, or in groupings or subsets. Similarly, dosage may be controlled by selectively activating various groupings or subsets of the ejection elements, or by some combination of firing rate and quantity control.

FIG. 4 is a schematic block diagram of a metered dose inhaler according to one embodiment of the present invention. As shown, inhaler 10 may include a controller 50 adapted to control inhaler 10 through electronic means, mechanical means, or both. Controller 50 thus may include a processor 52 and memory 54 configured to store preprogrammed physician-selected, pharmacist-selected, and/or user-selected operating parameters. Memory 54 may include volatile memory, nonvolatile memory, or both. User inputs, such as those indicated at 22 and 24 typically communicate with controller 50, among other things, to provide processor 52 with information/direction regarding the dosage of medicament to be produced.

It is to be appreciated that such information/direction may be provided via direct user input (as depicted in FIGS. 1 and 2), or may occur via a personal computer (or other device) configured to facilitate programming of controller 50 by a physician or pharmacist. The controller may provide a prescribed dosage or nominal dosage, and/or may be provided with dosage change parameters such as a loading dosage and/or a dosing regimen set by the physician, pharmacist, or manufacturer of the prescribed medicament. Such dosage regimen may be defined by a dosage ramp (linear, parametric or otherwise) defining progressive dosages (increasing and/or decreasing) for administering in successive dosing events. The dosing regimen also may be defined by a table of dosages, or some other quantification of medicament to be administered (e.g., dosage change percentage). The dosage thus may begin at some loading (typically a percentage of the prescription dosage), and then increase to the prescription dosage. After some predetermined number of dosing events, dosage may gradually be decreased.

The controller (and/or personal computer) also may be configured to provide for some form of security check prior to programming or dosing. For example, the controller may require input of a patient identification number, a physician identification number and/or prescription information. Such information may then be compared to information taken from the medication (e.g., by reading a barcode on the medication packaging), or to information in an associated database, prior to accepting any programming change. Programming by the physician or pharmacist also may be restricted by parameters set by the manufacturer of the prescribed medicament. Similarly, programming and/or dosing changes by the patient may be restricted by parameters set by the prescribing physician, the pharmacist, and/or the manufacturer of the prescribed medicament.

Various other input mechanisms also may be provided, such as sensor 56, which provides the controller with information regarding the level of medicament within medicament storage chamber 16. In the depicted embodiment, dosage information as well as other desired information may be communicated to display 26 for selected display.

As indicated, controller 50 also may be in electronic communication with ejection mechanism 14 so as to provide controlling direction to vaporization elements 46. Typically, such direction comes in the form of a transmission of an electronic signal 58 to one or more vaporization elements to effect activation of such element(s), and thus, to effect independently-controlled ejection of vaporized droplets of medicament as described with respect to FIG. 3. The character and frequency of such electronic signals may be determined by processor 52 based on the desired dosage to be produced. The desired dosage, in turn, may be defined by user input, by pre-programmed parameters, or by adaptive controller programming as described herein.

Accordingly, processor 52 may direct transmission by controller 50 of a single pulse to one or more of the vaporization elements so as to effect a single firing of an array of vaporization elements, and correspondingly, to produce a single array of vaporized droplets of medicament. Alternatively, the controller may transmit a series of rapid-succession pulses so as to successively activate one or more of the vaporization elements, thereby producing a longer duration "puff" of medicament vapor droplets than that previously mentioned.

Thus, when a user depresses or otherwise activates the activation input 22, processor 52 typically determines whether the requested dosage is appropriate, and if it is, controller 50 sends an appropriate ejection signal to at least one vaporization element 46. Upon receipt of an ejection signal, each vaporization element produces a vaporized droplet of medicament, for example, by generating sufficient heat as described above. Typically, the force of the an expanding change of medicament within an associated vaporization chamber is sufficient to successfully eject the vaporized droplet of medicament from the vaporization chamber.

As indicated previously, the duration, intensity, and/or other characteristic of the electronic signal may be altered to effect changes in the medicament dosage and/or ejection characteristic. Processor 52 thus may be configured, for example, to determine whether and how electronic signal 58 should be altered in response to a request from the user to increase or decrease the dosage, or dosing regimen. Similarly, processor 52 may be configured to determine whether and how to alter electronic signal 58 in response to a request from a physician, pharmacist or patient to alter permissible dosage or dosage regimen.

Inhaler 10 may further include a power supply (not shown). The power supply may be a battery or other suitable power supply, whether disposable or permanent. In some cases it may be desirable for the power supply to be a replenishable power supply, such as a rechargeable battery.

As indicated previously, the metered dose inhaler of the present embodiment of the invention may be adapted to produce droplets within a consistent size range by controlling the effective size and shape of the vaporization chambers and ejection orifices, and the characteristics of the electronic signals. Because consistent droplet size can be produced as a function of the characteristics of the vaporization chambers, ejection orifices and electronic signals, careful selection of the vaporization orifice characteristics and/or of the electronic signal allows the present inhaler to reliably produce droplets having diameters within a desired range. The desired diameter may vary depending on the intended use, and the particular medication, but typically is between 5 and 8 micrometers.

FIG. 5 is a flow chart illustrating a method of administering a medicament to a patient, the method being indicated generally at 60. At 62, a medicament dosage is selected. Such dosage may be selected by a prescribing physician, or by a pharmacist or other health professional in accordance with prescribing physician instructions (and/or in accordance with the manufacturer/supplier of the medicament). Such dosage may be recorded in memory of the inhaler's controller, and may be inaccessible to the patient. Alternatively, dosage may be selected by user input (e.g., user input 24), and altered, as needed, by the patient within parameters set by the pharmacist, the prescribing physician and/or the manufacturer/supplier of the medicament.

At 64, the medicament may be exposed to a vaporization element, typically by charging a vaporization chamber containing such vaporization element with a charge of medicament. The medicament is contained in the vaporization chamber, typically by surface adhesion caused by a meniscus as described above. As will be appreciated, the inhaler typically will include a plurality of vaporization chambers, each chargeable with a charge of medicament and each independently dischargeable via an associated vaporization element.

At 66, electronic signals based on the selected dosage are transmitted to the vaporization element(s). As indicated previously, such electronic signals may vary in frequency, destination, and/or characteristic in order to achieve the desired dosage as selected above. Correspondingly, the frequency, destinations and/or characteristics of such electronic signals may be varied by the controller in accordance with altered dosage directives.

The electronic signals activate the respective vaporization element(s) at 68. Such activation typically includes heating the vaporization element sufficient to urge a vaporized droplet of medicament through an orifice in the corresponding vaporization chamber. Medicament in the vicinity of the vaporization element typically is superheated in response to an electronic signal so as to produce a bubble which expands toward an ejection orifice, forcing more distal medicament toward the ejection orifice. Correspondingly, therefore, at 70, medicament may be ejected through the ejection orifice(s) in vaporized droplet form such that the user can respire the vaporized droplet(s) of medicament.

Figure 6:
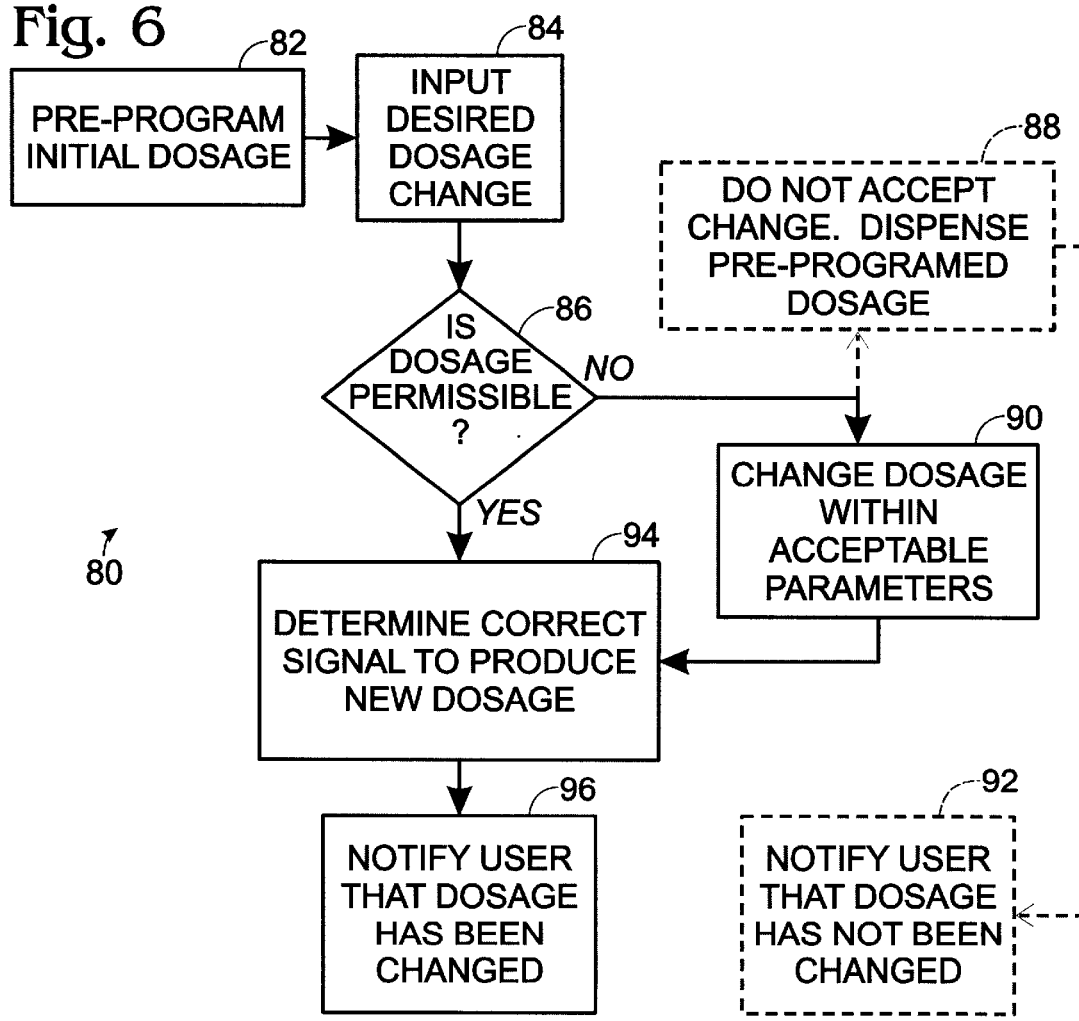
FIG. 6 is a flow chart illustrating methodology by which a dosage administered by a metered dose inhaler may be altered.

FIG. 6 depicts, at 80, one possible method by which the controller may alter dosage levels based on user input. The controller processor may be pre-programmed (for example by a physician or pharmacist) with an initial dosage at 82. Correspondingly, the physician or pharmacist may pre-program parameters within which the dosage may be altered. Such pre-programming may involve, for example, directly entering prescription information such as a patient identification number, entering a physician identification number, and entering a prescription (including dosage, and dosage change parameters). This information then may be compared to related security check information (e.g. read from a barcode on the actual medication and/or stored within an associated database). If the directly entered prescription information is compatible with the indirectly entered security check information, the inhaler may be configured to perform in accordance with the prescription. If the entered information is not compatible with the security check information, the inhaler may be configured to produce an error message to that effect.

When desired, the patient may input or select a desired dosage change at 84, for example, by indicating whether the user desires the dosage to be increased or decreased via a user input such as that shown at 24 in FIG. 1. Alternatively, a desired dosage change may be selected simply by indicating a desired dosage. To this end, the inhaler may provide the patient with input mechanisms to indicate the desired dosage.

Once the user has selected the desired dosage, the processor may determine, at 86, whether the desired dosage falls within specified acceptable parameters. If the patient's desired dosage is outside of the acceptable parameters, the processor may either reject the dosage completely at 88 (keeping the original dosage), or change the dosage as much as possible while still remaining inside the acceptable parameters at 90. If the dosage is not changed, the patient may be so-notified as indicated at 92.

Once the processor has determined what the new dosage should be, the processor may determine the ejection signals effective to administer the new dosage, at 94. As explained above, this may be accomplished, for example, by adjusting the frequency of ejection signals sent to the vaporization element, adjusting the characteristics of the signals sent to the vaporization element, and/or adjusting the quantity of vaporization elements activated. In addition, as indicated at 96, it may be desirable to notify the patient that the dosage has been altered and what the current dosage is, for example, via display 26.

As will be appreciated, in some circumstances it may be desirable to restrict user control over dosage beyond certain limits. Thus, the processor may be configured with various safety parameters. These safety parameters may control, for example, the maximum dosage, the minimum dosage, the maximum number of doses within a specified time period, and/or the expiration date of the medication. Each of these parameters may be dependent upon the type of medication and the patient. These safety parameters may be set during manufacture of the metered dose inhaler, or may be input by a physician or pharmacist prior to dispensing the metered dose inhaler to the patient.

Alternatively or additionally, the processor may be configured to alter the dosage released by the metered dose inhaler during a dosage regimen. For example, in some cases it may be desirable to gradually increase or gradually decrease the dosage during a course of treatment. In some cases it may be desirable to administer a loading dosage, wherein the initial dosage is greater than the remaining dosages. This loading dosage may immediately raise the concentration of medication in the patent's body to the projected steady-state value, and then use the remaining dosage to maintain the steady-state level of medication in the patient. Loading dosages are typically used where the physician determines that a loading dosage of a particular medication does not pose significant risks to the health of the patient and where it is imperative that the target level of medication in the patient is achieved in a minimum amount of time.

FIG. 7 is a flow chart demonstrating a method, at 100, by which a physician or pharmacist may regulate a patient's dosing regimen. This information may be provided upon pre-programming the inhaler, or subsequently upon recharging the inhaler, or otherwise servicing the inhaler. The depicted method begins with the identification of the prescribed dosage (or nominal dosage) for a given medication at 102, but it will be appreciated that the depicted ordering of steps is not required. At 104, the physician or pharmacist may select one of several options including: a fixed dosage, a loading dosage, or a controlled rate-of-change dosage. If the physician selects a fixed dosage, the dosage selection process is complete at 106. If the physician/pharmacist selects a loading dosage, a loading dosage is identified at 108, and the dosage selection process is complete at 106. If the physician/pharmacist selects a controlled rate-of-change dosage, the physician/pharmacist may identify whether he/she desires the dosage to ramp up or ramp down at 110. The physician/pharmacist may then select either a parametric dosage ramp or linear dosage ramp at 112. If a linear dosage ramp is selected, the physician may enter the slope of the ramp at 114. If a parametric dosage ramp is selected, the physician/pharmacist may, at 116, enter the selected values for the various dosage levels, for example, as percentages of the maximum dosage. These values also may include a progression of such dosages (e.g., over successive dosing events, or over a prescribed time). Once the appropriate information is entered, the dosage selection routine is complete at 106. The medication thus may be dispensed in accordance with the identified dosages at 118.

As will be appreciated, in some cases it may be undesirable to allow the patient to alter the dosage of a particular medication. In this case, the inhaler may include a lockout mechanism that prevents the patient from altering the dosage while still allowing the physician or pharmacist to make any necessary changes. For example, altering the inhaler regimen may require specific software, hardware, etc., available only to physicians and/or pharmacists. Alternatively password protection or other suitable security measures may be employed.

Furthermore, the processor may be configured to take a wide variety of factors into consideration when determining the proper dosage. For example, processor 52 may be configured to determine the medication's half-life (possibly entered by the pharmacist or physician at the time of pre-programming) and increase dosage over time accordingly. Alternatively, processor 52 may be configured to determine the patient's past dosing behavior and determine safe levels of increased or decreased dosages when a patient has missed a dosage or administered a dosage incorrectly.

The present invention provides a metered dose inhaler adapted to solve many of the problems identified with previously described metered dose inhalers. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements. It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

What is claimed is:

1. A metered dose inhaler comprising:
   an ejection mechanism including a plurality of vaporization chambers configured to contain a medicament, the ejection mechanism being configured to selectively effect controlled ejection of medicament from the plurality of vaporization chambers; and
   a controller configured to selectively send electronic signals to the ejection mechanism to direct ejection of medicament from a plurality of vaporization chambers, such electronic signals being selectively alterable to effect change in medicament dosage.

2. The metered dose inhaler of claim 1, which further comprises an input in communication with the controller to identify a dosage of medicament ejected by the ejection mechanism.

3. The metered dose inhaler of claim 1, wherein the controller is further configured to receive a nominal dosage and one or more dosage change parameters.

4. The metered dose inhaler of claim 3, wherein the dosage change parameters are set by a manufacturer of the medicament.

5. The metered dose inhaler of claim 3, wherein the dosage change parameters are set by a prescribing physician.

6. The metered dose inhaler of claim 3, wherein the one or more dosage change parameters includes a permissible dosage, and wherein the controller is further configured to restrict dosage change to such permissible dosage.

7. The metered dose inhaler of claim 3, wherein the one or more dosage change parameters includes a loading dosage, and wherein the controller is further configured to direct ejection of the loading dosage of medicament in a first dosing event followed by ejection of the nominal dosage of medicament in a second dosing event.

8. The metered dose inhaler of claim 3, wherein the one or more dosage change parameters includes a dosing ramp, and wherein the controller is further configured to direct ejection of progressive dosages of medicament along such dosing ramp in successive dosing events.

9. The metered dose inhaler of claim 8, wherein the dosing ramp is based on medicament half-life.

10. The metered dose inhaler of claim 8, wherein the dosing ramp is based on patient dosing behavior.

11. The metered dose inhaler of claim 8, wherein the dosing ramp is a look-up table of dosages to be administered.

12. The metered dose inhaler of claim 8, wherein the progressive dosages of medicament along such dosing ramp are increasing dosages.

13. The metered dose inhaler of claim 8, wherein the dosing ramp is linear.

14. The metered dose inhaler of claim 1, wherein the controller is further configured, and to set a frequency of the electronic signals in accordance with such prescribed dosage.

15. The metered dose inhaler of claim 1, wherein the controller is further configured, and to select a size of a subset of vaporization elements receiving the electronic signals in accordance with such prescribed dosage.

16. A metered dose inhaler adapted to release a selectable quantity of an inhalant into a body of a user, the metered dose inhaler comprising:
   a storage chamber containing an inhalant;
   a plurality of ejection chambers, each in respective fluid communication with the storage chamber to accommodate charging of such ejection chambers with inhalant from the storage chamber, each ejection chamber further including at least one ejection element configured to selectively eject a charge of inhalant from within the ejection chamber upon receipt of an ejection signal; and
   a controller adapted to receive a dosage directive, and to transmit ejection signals to the ejection elements to effect release of a prescribed dosage of inhalant via independently controlled ejection of charges of inhalant from such plurality of ejection chambers in a dosing event.

17. The metered dose inhaler of claim 16, wherein the controller is further adapted to receive one or more dosage change parameters.

18. The metered dose inhaler of claim 17, wherein the dosage change parameters are set by a manufacturer of the inhalant.

19. The metered dose inhaler of claim 17, wherein the dosage change parameters are set by a prescribing physician.

20. The metered dose inhaler of claim 17, wherein the one or more dosage change parameters includes a permissible dosage, and wherein the controller is further configured to restrict dosage change to such permissible dosage.

21. The metered dose inhaler of claim 17, wherein the one or more dosage change parameters includes a loading dosage, and wherein the controller is further adapted to direct release of the loading dosage of inhalant in a first dosing event followed by release of the prescribed dosage of inhalant in a second dosing event.

22. The metered dose inhaler of claim 17, wherein the one or more dosage change parameters includes a dosing ramp, and wherein the controller is further configured to direct release of progressive dosages of inhalant along such dosing ramp in successive dosing events.

23. The metered dose inhaler of claim 22, wherein the dosing ramp is based on inhalant half-life.

24. The metered dose inhaler of claim 22, wherein the dosing ramp is based on patient dosing behavior.

25. The metered dose inhaler of claim 22, wherein the dosing ramp is a look-up table of dosages to be administered.

26. The metered dose inhaler of claim 16, further comprising a user input in communication with the controller, the user input being configured to facilitate communication between the user and the controller.

27. The metered dose inhaler of claim 26, wherein the user input is configured to communicate a firing directive from the user to the controller to initiate a dosing event.

28. The metered dose inhaler of claim 26, which further comprises a display configured to communicate information to the user.

29. A method of administering a medicament to a patient comprising:
   providing a dose directive indicative of a dosage of medicament to a controller
   charging a plurality of vaporization chambers with a charge of medicament so as to expose medicament to a plurality of vaporization elements contained within the plurality of vaporization chambers;
   selectively transmitting electronic signals to a plurality of vaporization elements in accordance with the received dosing directive; and
   upon receipt of the electronic signals, activating the vaporization elements so as to discharge vaporized droplets of medicament from the associated vaporization chambers to produce the dosage of medicament indicated by the dosing directive.

30. The method of claim 29, which further comprises setting dosage change parameters in accordance with manufacturer directives.

31. The method of claim 29, which further comprises setting dosage change parameters in accordance with physician directives.

32. The method of claim 29, which further comprises changing dosage, in successive dosing events, according to a look-up table of successive dosages to be administered.

33. The method of claim 29, which further comprises changing dosage, in successive dosing events, according to a dosing ramp.

34. The method of claim 29, which further comprises changing dosage, in successive dosing events, where dosing ramp is based on medicament half-life.

35. The method of claim 29, which further comprises changing dosage, in successive dosing events, where dosing ramp is based on patient dosing behavior.

36. The method of claim 29, which further comprises altering a frequency of the electronic signals so as to alter the dosage of medicament produced during a dosing event, including multiple different dosages that change according to a pre-programmed schedule.

37. The method of administering a medicament to a patient comprising:
   entering prescription information;
   entering security check information;
   verifying compatibility of the prescription information with the security check information.
   providing a dosing directive indicative of a medicament;
   charging at least one vaporization chamber with a charge of medicament so as to expose medicament to one or more vaporization elements contained within the at least one vaporization chamber;
   selectively transmitting electronic signals to the one or more vaporization elements in accordance with the received dosing directive; and
   upon receipt of the electronic signals, activating the vaporization elements so as to discharge vaporized droplets of medicament from the associated vaporization chambers to produce the dosage of medicament indicated by the dosing directive.

38. The method of claim 37, wherein entering prescription information includes direct entry of one or more of a patient identification, a physician identification, and a medicament identification.

39. The method of claim 38, wherein entering security check information includes indirect entry of one or more of a patient identification, a physician identification, and a medicament identification.

40. A method of administering a medicament to a patient comprising:
   providing a dosing directive indicative of a dosage of medicament;
   charging at least one vaporization chamber with a charge of medicament so as to expose medicament to one or more vaporization elements contained within the at least one vaporization chamber;

selectively transmitting electronic signals to the one or more vaporization elements in accordance with the received dosing directive; and upon receipt of the electronic signals, activating the vaporization elements so as to discharge vaporized droplets of medicament from the associated vaporization chambers to produce the dosage of medicament indicated by the dosing directive;

wherein selectively transmitting electronic signals included transmitting electronic signals to a subset of vaporization elements so as to discharge vaporized droplets of medicament from a corresponding subset of vaporization chambers.

41. The method of claim 40, which further comprises altering the subset of vaporization chambers so as to alter the dosage of medicament produced during a dosing event.

42. The method of administering a dosage of a medicament to a patient, the method comprising:

exposing a volume of a medicament to a plurality of ejection elements;

selecting a nominal dosage of medicament to be ejected;

transmitting an ejection signal to at least one of the ejection elements, wherein the ejection signal is determined based on the selected nominal dosage; and ejecting vaporized droplets of medicament from adjacent the ejection elements for respiration by the patient, dosage of medicament ejected being determined, at least in part, by frequency and quantity of ejection signals received by the ejection elements during a nominal dosage event.

43. A method of claim 42, which further comprises selecting a loading dosage, transmitting a loading ejection signal to at least one of the ejection elements based on such loading dosage, and ejecting vaporized droplets of medicament corresponding to such loading ejection signal in a loading dosage event, such loading dosage event preceding the dosing event.

44. The method of claim 42, which further comprises selecting a dosing ramp, determining progressive dosages along such dosing ramp, transmitting ejection signals based on such progressive dosages in successive dosing events, and in connection with each successive dosing event, ejecting vaporized droplets of medicament corresponding to the ejection signals of such dosing event.

45. A metered dose inhaler comprising: an ejection mechanism including at least one vaporization chamber configured to contain a medicament, the ejection mechanism being configured to selectively effect controlled ejection of medicament from the at least one vaporization chamber; and a controller configured to selectively send electronic signals to the ejection mechanism to direct ejection of medicament from the at least one vaporization chamber, such electronic signals being selectively alterable to effect change in medicament dosage, the controller further being configured to receive a nominal dosage, a prescribed dosage, and one or more dosage change parameters which effect a desired medicament delivery schedule that includes multiple different dosages which change according to a pre-programmed schedule, and wherein the controller is further configured a prescribed dosage, and to select a subset of plural vaporization elements receiving the electronic signals in accordance with such prescribed dosage.

46. A metered dose inhaler of claim 45, which further comprises an input in communication with the controller to identify the nominal dosage.

47. A metered dose inhaler of claim 45, wherein the one or more dosage change parameters includes a permissible dosage, and wherein the controller is further configured to restrict dosage according to such permissible dosage.

48. A metered dose inhaler of claim 45, wherein the one or more dosage change parameters includes a loading dosage, and wherein the controller is further configured to direct ejection of the loading dosage of medicament in a first dosing event followed by ejection of the nominal dosage of medicament in a second dosing event.

49. A metered dose inhaler of claim 45, wherein the one or more dosage change parameters includes a dosing ramp, and wherein the controller is further configured to direct ejection of progressive different dosages of medicament along such dosing ramp in successive dosing events.

50. The metered dose inhaler of claim 45, wherein the controller is further configured to receive prescription information for comparison to security check information, and to restrict changes in medicament dosage based on such comparison.

* * * * *

UNITED STATES PATENT AND TRADEMARK OFFICE
CERTIFICATE OF CORRECTION

PATENT NO.    : 6,830,046 B2
DATED         : December 14, 2004
INVENTOR(S)   : Blakley et al.

It is certified that error appears in the above-identified patent and that said Letters Patent is hereby corrected as shown below:

Column 10,
Line 22, delete "dosage." and insert therefor -- dosage; wherein the controller is configured to receive a prescribed dosage, and to select a subset of plural vaporization chambers receiving the electronic signals in accordance with such prescribed dosage. --
Lines 63 and 67, delete "configured, and" and insert therefor -- configured --.

Column 11,
Line 63, delete "controller" and insert therefor -- controller; --.

Column 12,
Line 8, delete "directive." and insert therefor -- directive and selecting a subset of plural vaporization elements receiving the electronic signals in accordance with such dosing directive. --.
Line 32, delete "The" and insert therefor -- A --.
Line 37, delete "information." and insert therefor -- information; --.

Column 13,
Line 10, delete "included" and insert therefor -- includes --.
Line 17, delete "The" and insert therefor -- A --.
Line 32, delete "A" and insert therefor -- The --.

Column 14,
Line 16, after "configured", insert -- to receive --.
Line 17, delete "dosage, and" and insert therefor -- dosage --.
Lines 20, 23, 27 and 34, delete "A" and insert therefor -- The --.

Signed and Sealed this

Twenty-eighth Day of June, 2005

JON W. DUDAS
*Director of the United States Patent and Trademark Office*